US012734329B2

(12) United States Patent
Levy et al.

(10) Patent No.: US 12,734,329 B2
(45) Date of Patent: Sep. 15, 2026

(54) GROOVED CATHETER WITH RECESSED IRRIGATION HOLES

(71) Applicant: Biosense Webster (Israel) Ltd., Yokneam (IL)

(72) Inventors: Tzachi Levy, Irvine, CA (US); Meir Bar-Tal, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 295 days.

(21) Appl. No.: 18/500,917

(22) Filed: Nov. 2, 2023

(65) Prior Publication Data

US 2024/0189545 A1 Jun. 13, 2024

Related U.S. Application Data

(60) Provisional application No. 63/387,130, filed on Dec. 13, 2022.

(51) Int. Cl.

| | |
|---|---|
| ***A61M 25/00*** | (2006.01) |
| ***A61B 18/00*** | (2006.01) |
| ***A61B 18/14*** | (2006.01) |

(52) U.S. Cl.

CPC ....... *A61M 25/007* (2013.01); *A61B 18/1492* (2013.01); *A61B 2018/00577* (2013.01); *A61B 2218/002* (2013.01)

(58) Field of Classification Search

None

See application file for complete search history.

(56) References Cited

U.S. PATENT DOCUMENTS

| | | | |
|---|---|---|---|
| 6,226,542 | B1 | 5/2001 | Reisfeld |
| 6,301,496 | B1 | 10/2001 | Reisfeld |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,536,218 | B2 | 5/2009 | Govari et al. |
| 7,756,576 | B2 | 7/2010 | Levin |
| 8,517,999 | B2 | 8/2013 | Pappone et al. |
| 9,579,148 | B2 | 2/2017 | Wang et al. |
| 9,737,353 | B2 | 8/2017 | Govari et al. |

(Continued)

OTHER PUBLICATIONS

Extended European Search Report and Opinion dated Apr. 15, 2024, from corresponding European Application No. 23215830.3.

*Primary Examiner* — Sean W Collins
*Assistant Examiner* — Nora W Rhodes

(57) ABSTRACT

Medical devices and methods of use thereof are disclosed. The medical device can include an elongated catheter body defining a longitudinal axis and a distal tip electrode coupled to a distal end of the elongated catheter body. The distal tip electrode can have an outer surface, a cavity, a proximal end, a distal end, and a wall having a plurality of apertures connecting the outer surface and the cavity, with apertures arranged in a grid. The wall of the distal tip electrode can have a plurality of longitudinal grooves and a plurality of circumferential grooves formed therein so that each longitudinal groove extends generally parallel to the longitudinal axis and has at least two apertures positioned with a respective longitudinal groove and each circumferential groove intersects with at least one of the longitudinal grooves to define an aperture at such intersection.

20 Claims, 9 Drawing Sheets

(56) References Cited

U.S. PATENT DOCUMENTS

| | | | | |
|---|---|---|---|---|
| 9,956,035 | B2 | 5/2018 | Govari et al. | |
| 10,327,859 | B2 | 6/2019 | Botzer et al. | |
| 2003/0009094 | A1 | 1/2003 | Segner et al. | |
| 2008/0249522 | A1 | 10/2008 | Pappone et al. | |
| 2010/0286684 | A1 | 11/2010 | Hata et al. | |
| 2011/0009857 | A1 | 1/2011 | Subramaniam et al. | |
| 2012/0035466 | A1 | 2/2012 | Tegg | |
| 2015/0272669 | A1* | 10/2015 | Brucker | A61B 18/1492 606/41 |
| 2016/0183821 | A1* | 6/2016 | Pai | A61B 5/283 604/21 |
| 2018/0104000 | A1* | 4/2018 | Beeckler | A61B 18/1492 |
| 2018/0369458 | A1 | 12/2018 | Mangual-Soto et al. | |
| 2021/0282848 | A1 | 9/2021 | Beeckler et al. | |

* cited by examiner

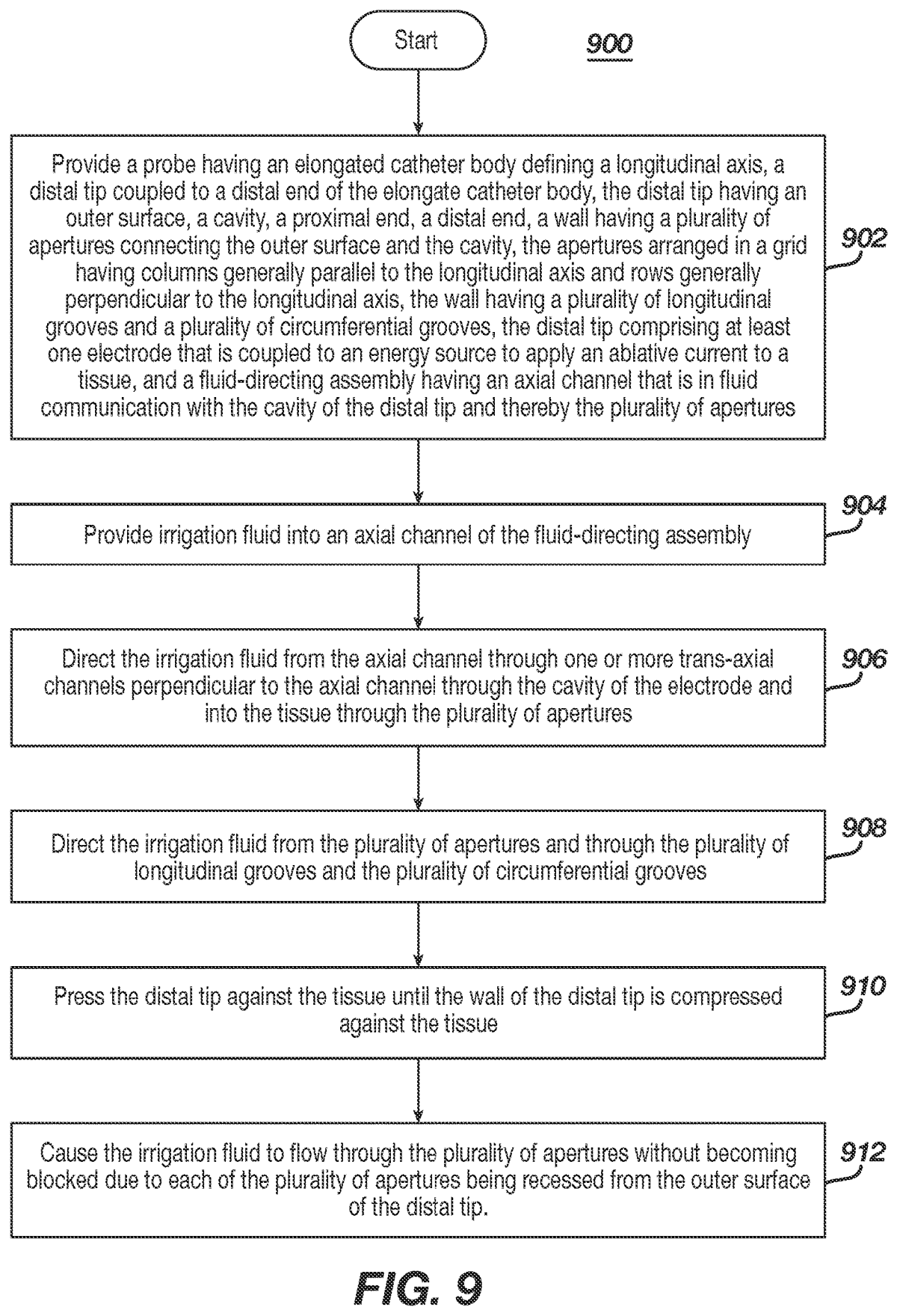

Start

900

902 Provide a probe having an elongated catheter body defining a longitudinal axis, a distal tip coupled to a distal end of the elongate catheter body, the distal tip having an outer surface, a cavity, a proximal end, a distal end, a wall having a plurality of apertures connecting the outer surface and the cavity, the apertures arranged in a grid having columns generally parallel to the longitudinal axis and rows generally perpendicular to the longitudinal axis, the wall having a plurality of longitudinal grooves and a plurality of circumferential grooves, the distal tip comprising at least one electrode that is coupled to an energy source to apply an ablative current to a tissue, and a fluid-directing assembly having an axial channel that is in fluid communication with the cavity of the distal tip and thereby the plurality of apertures 904 Provide irrigation fluid into an axial channel of the fluid-directing assembly 906 Direct the irrigation fluid from the axial channel through one or more trans-axial channels perpendicular to the axial channel through the cavity of the electrode and into the tissue through the plurality of apertures 908 Direct the irrigation fluid from the plurality of apertures and through the plurality of longitudinal grooves and the plurality of circumferential grooves 910 Press the distal tip against the tissue until the wall of the distal tip is compressed against the tissue 912 Cause the irrigation fluid to flow through the plurality of apertures without becoming blocked due to each of the plurality of apertures being recessed from the outer surface of the distal tip.

FIG. 9

GROOVED CATHETER WITH RECESSED IRRIGATION HOLES

CROSS-REFERENCE TO RELATED APPLICATIONS

This application claims the benefit of prior filed U.S. Provisional Patent Application No. 63/387,130 filed on Dec. 13, 2022, which is hereby incorporated by reference as set forth in full herein.

FIELD

This invention relates to devices that introduce media into the body. More particularly, this invention relates to an ablation catheter having side holes for passage of fluid therethrough.

BACKGROUND

In some medical procedures, energy is imparted to body tissue locally, in a concentrated dose, and it is desirable to cool the treatment area in order to reduce collateral tissue damage.

A known difficulty in the use of radiofrequency energy for cardiac tissue ablation is controlling overheating of tissue at the treatment site. There are tradeoffs between the desire to create a sufficiently large lesion to effectively ablate an abnormal tissue or block an aberrant conduction pattern, and the undesirable effects of overheating areas proximal to the treatment site. If the radiofrequency device creates to small a lesion, the medical procedure could be less effective or could require too much time. On the other hand, if the tissue is heated excessively there could be local charring effects, coagulum, and team pops due to overheating. Such overheated areas can develop high impedance, and may form a functional barrier to the passage of heat. The use of slower heating provides better control of the ablation, but unduly prolongs the procedure.

It has been found that cooling the area of the ablation site reduces tissue charring and thrombus formation. For this purpose, Biosense Webster Inc. (Diamond Bar, California) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

For example, U.S. Pat. No. 8,517,999 to Pappone et al., describes an irrigated catheter with uniform cooling and/or uniform fluid distribution in longitudinally spaced apart elution holes by varying the diameter of a fluid delivery lumen. A number of elution holes are provided in a tip region of a catheter body, and these elution holes are in fluid communication with the lumen through ducts.

SUMMARY

Medical devices and methods of use thereof are disclosed. The medical device can include an elongated catheter body defining a longitudinal axis and a distal tip electrode coupled to a distal end of the elongated catheter body. The distal tip electrode can have an outer surface, a cavity, a proximal end, a distal end, and a wall having a plurality of apertures connecting the outer surface and the cavity, with apertures arranged in a grid. The wall of the distal tip electrode can have a plurality of longitudinal grooves and a plurality of circumferential grooves formed therein so that each longitudinal groove extends generally parallel to the longitudinal axis and has at least two apertures positioned with a respective longitudinal groove and each circumferential groove intersects with at least one of the longitudinal grooves to define an aperture at such intersection.

An aspect of the present invention that is described herein provides for a medical device. The medical device may include an elongated catheter body that defines a longitudinal axis. The medical device may include a distal tip electrode that is coupled to a distal end of the elongated catheter body. The distal tip electrode can have an outer surface, a cavity, a proximal end, a distal end, and a wall having a plurality of apertures connecting the outer surface and the cavity. The apertures can be arranged in a grid with columns generally parallel to the longitudinal axis and rows that are generally perpendicular to the longitudinal axis. The medical device may include a plurality of longitudinal grooves formed in the wall of the distal tip electrode so that each longitudinal groove extends generally parallel to the longitudinal axis. Each of the plurality of longitudinal grooves can have at least two apertures of the plurality of apertures positioned within a respective longitudinal groove. The medical device can include a first plurality of circumferential grooves formed in the wall of the distal tip electrode so that each circumferential groove intersect with at least one of the longitudinal grooves to define an aperture at such intersection.

According to some embodiments, the medical device can further include one more sensing elements disposed on the distal end of the distal tip electrode. Each of the one or more sensing elements can be positioned between two adjacent longitudinal grooves.

According to some embodiments, each of the plurality of apertures can be recessed from the outer surface of the distal tip electrode by a distance D. According to some embodiments, the distance D may be between approximately 0.05 mm and 0.02 mm.

According to some embodiments, a first portion of the plurality of apertures can be oriented at a proximal angle with respect to the longitudinal axis. The first portion can be positioned on a row proximate the proximal end of the distal tip electrode.

According to some embodiments, a second portion of the plurality of apertures are oriented at a distal angle with respect to the longitudinal axis. The second portion can be positioned on a row proximate the distal end of the distal tip electrode.

According to some embodiments, the apertures can be configured to direct an irrigation fluid.

According to some embodiments, the first plurality of circumferential grooves can have at least two apertures of respective non-adjacent columns positioned within a respective circumferential groove of the first plurality of circumferential grooves.

According to some embodiments, the plurality of longitudinal grooves can have four apertures positioned within a respective longitudinal groove.

According to some embodiments, the plurality of longitudinal grooves and the first plurality of circumferential grooves can form a gird-pattern on the wall of the distal tip electrode.

According to some embodiments, the medical device can further include a fluid directing assembly having an axial channel in fluid communication with the cavity of the distal tip electrode and thereby the plurality of apertures. The medical device an also include a blocking terminus that is fixed within the cavity of the distal tip electrode. The blocking terminus can be configured to block a flow of fluid in a longitudinal direction and to direct the flow of fluid through at least one trans-axial channel that is transverse to the axial channel and to direct the flow of fluid through the plurality of apertures. According to some embodiments, the fluid-directing assembly can have between two and twelve trans-axial channels. According to some embodiments, the fluid-directing assembly can have exactly one trans-axial channel.

According to some embodiments, the distal tip electrode can include at least one electrode coupled to an energy source to apply an ablative current to a tissue. The fluid-directing assembly can be in fluid communication with an irrigation pump that delivers irrigation fluid to the fluid-directing assembly, and in response to increasing power to the at least one electrode to approximately 90 W, the medical device can increase an irrigation flow rate of the irrigation pump. According to some embodiments, the irrigation flow rate can be increased by closing a loop with the irrigation pump.

In another aspect, a medical device is disclosed. The medical device can include an elongated catheter body defining a longitudinal axis. The medical device can include a distal tip coupled to a distal end of the elongated catheter body. The distal tip can have an outer surface, a cavity, a proximal end, a distal end, and a wall having a plurality of apertures connected to the outer surface and the cavity. The distal tip can include at least one electrode coupled to an energy source. The electrode can be configured to apply an ablative current to a tissue inside a body of a patient. The wall of the distal tip can have a first plurality of grooves formed therein. Each of the first plurality of grooves can be formed in a first orientation with respect to the longitudinal axis. The wall of the distal tip can include a second plurality of grooves formed therein. The second plurality of grooves can be formed in a second orientation with respect to the longitudinal axis. Each of the first plurality of grooves and the second plurality of grooves can have at least two respective apertures of the plurality of apertures positioned within a respective groove. The medical device can include a fluid-directing assembly. The fluid-directing assembly can have an axial channel that is in fluid communication with the cavity of the distal tip and thereby the plurality of apertures. The medical device can also include a blocking terminus that is fixed within the cavity of the distal tip. The blocking terminus can be configured to block the flow of fluid in the longitudinal direction and direct the flow of fluid through at least one trans-axial channel that is transverse to the axial channel.

According to some embodiments, the first plurality of grooves and the second plurality of grooves each can form diagonal grooves with respect to the longitudinal axis in the wall of the distal tip.

According to some embodiments, the first plurality of grooves and the second plurality of grooves can be arranged in a mesh pattern of grooves in the wall of the distal tip.

According to some embodiments, the first plurality of grooves and the second plurality of grooves can be arranged in a randomized pattern in the wall of the distal tip.

According to some embodiments, the medical device can include one or more sensing elements disposed on the distal tip.

According to some embodiments, the fluid-directing assembly can be in fluid communication with an irrigation pump that delivers irrigation fluid to the fluid-directing assembly. In response to increasing power to the at least one electrode to approximately 90 W, the medical device can increase an irrigation flow rate of the irrigation pump.

According to some embodiments, each of the plurality of apertures can be recessed from the outer surface of the distal tip by a distance D. According to some embodiments, the distance D can be between approximately 0.05 mm and 0.2 mm.

According to some embodiments, a first portion of the plurality of apertures can be oriented at a proximal angle with respect to the longitudinal axis. The first portion of the plurality of apertures can be positioned on a row proximate the proximal end of the distal tip. According to some embodiments, a second portion of the plurality of apertures can be oriented at a distal angle with respect to the longitudinal axis. The second portion of apertures of the plurality of apertures can be positioned on a row proximate the distal end of the distal tip.

According to some embodiments, the apertures can be configured to direct an irrigation fluid to a tissue inside the body.

In another aspect, a method of directing irrigation fluid from a medical probe is disclosed. The method can include providing a probe having an elongated catheter body defining a longitudinal axis, a distal tip coupled to a distal end of the elongate catheter body, and a fluid directing assembly having an axial channel that is in fluid communication with a cavity within the distal tip and a plurality of apertures that connect an outer surface of the distal tip with the cavity. The distal tip can have an outer surface, a cavity, a proximal end, a distal end, and a wall having a plurality of apertures connecting the outer surface and the cavity. The apertures can be arranged in a grid having columns generally parallel to the longitudinal axis and rows generally perpendicular to the longitudinal axis. The wall can have a plurality of longitudinal grooves and a plurality of circumferential grooves. The distal tip can include at least one electrode that is coupled to an energy source that can be configured to apply an ablative current to a tissue. The method can include providing irrigation fluid into an axial channel of the fluid-directing assembly. The method can include directing the irrigation fluid from the axial channel through one or more trans-axial channels perpendicular to the axial channel through the cavity of the electrode and into the tissue through the plurality of apertures. The method can include directing the irrigation fluid from the plurality of apertures and through the plurality of longitudinal grooves and plurality of circumferential grooves.

According to some embodiments, a first portion of the plurality of apertures can be oriented at a proximal angle with respect to the longitudinal axis. The first portion of the plurality of apertures can be positioned on a row that is proximate the proximal end of the distal tip. According to some embodiments, a second portion of the plurality of apertures can be oriented at a distal angle with respect to the longitudinal axis. The second portion of the plurality of apertures can be positioned on a row that is proximate the distal end of the distal tip.

According to some embodiments, each of the plurality of apertures can be recessed from the outer surface of the distal tip by a distance D. According to some embodiments, the distance D is between approximately 0.05 mm and approximately 0.2 mm.

According to some embodiments, the method can include pressing the distal tip against the tissue until the wall of the distal tip is compressed against the tissue and causing irrigation fluid to flow through the plurality of apertures without becoming blocked due to each of the plurality of apertures being recessed from the outer surface of the distal tip.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 9 is a flowchart of an exemplary method of treating a patient using a catheter according to aspects of the present invention.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient." "host." "user," and "subject" refer to any human or animal subject and are not intended to limit the systems or methods to human use, although use of the subject invention in a human patient represents a preferred embodiment.

Figure 1:
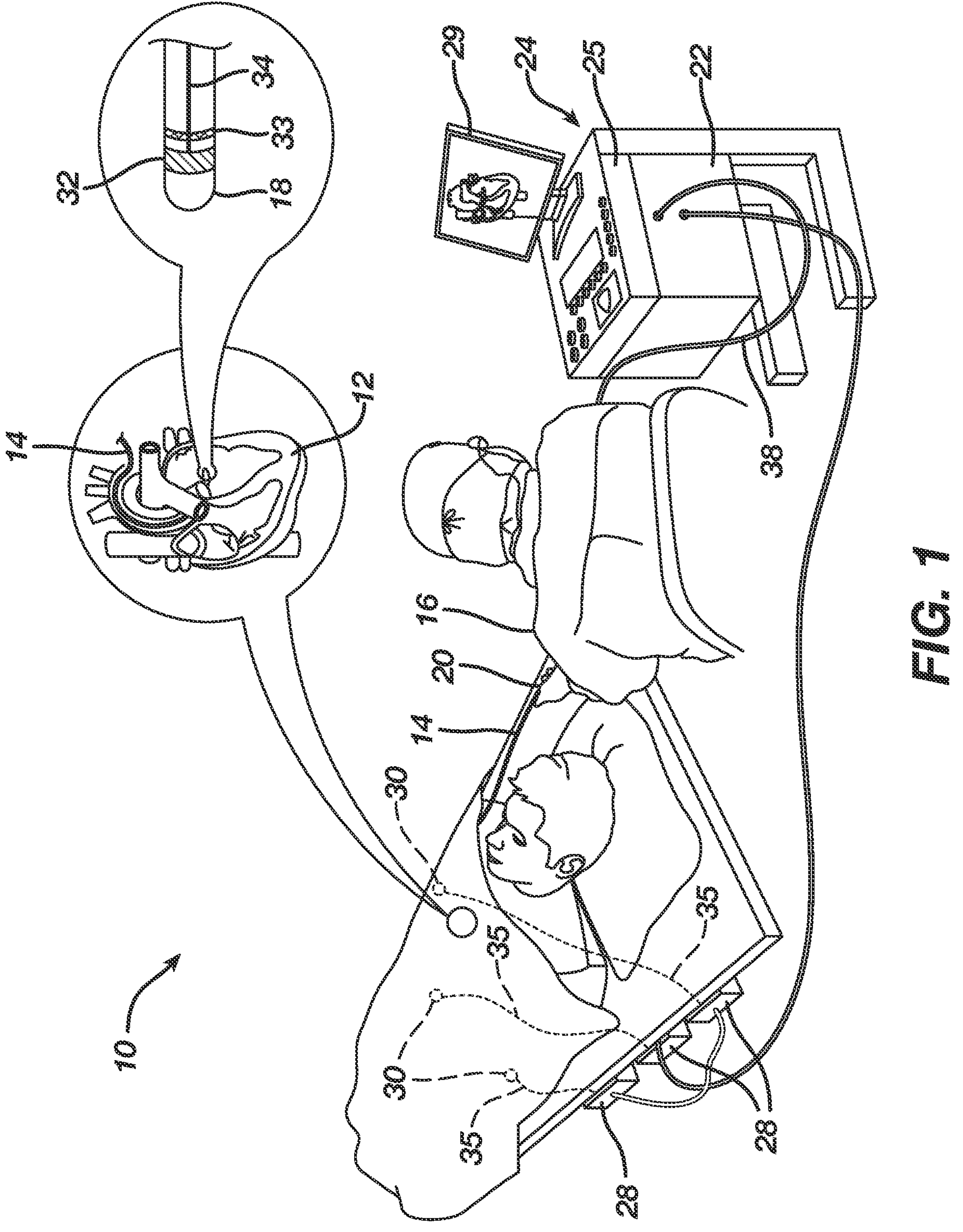
FIG. 1 is an illustration of a cardiovascular treatment utilizing a catheter, according to aspects of the present invention.

As shown in FIG. 1 system 10 may be utilized for evaluating electrical activity and performing ablative procedures on a heart 12 of a living subject, which is constructed and operative in accordance with a disclosed embodiment of the invention. The system includes a catheter 14, which is percutaneously inserted by an operator 16 through the patient's vascular system into a chamber or vascular structure of the heart 12. The operator 16, who is typically a physician or medical professional, brings the catheter's distal tip 18 into contact with the heart wall, for example, at an ablation target site. Electrical activation maps may be prepared, according to the methods disclosed in U.S. Pat. Nos. 6,226,542 and 6,301,496, in commonly assigned U.S. Pat. No. 6,892,091, and U.S. Patent Pub. No. 2021/0282848, whose disclosures are herein incorporated by reference, and attached to the Appendix of priority patent Application No. 63/387,130. One commercial product embodying elements of the system 10 is available as the CARTO® 3 System, available from Biosense Webster, Inc., 3333 Diamond Canyon Road, Diamond Bar, CA 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupts the abnormal electrical pathway causing the arrhythmia. The principles of the invention can be applied to different heart chambers to diagnose and treat many different cardiac arrhythmias.

Catheter 14 typically includes a handle 20, having suitable controls on the handle to enable the operator 16 to steer, position, and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference as if recited in full, and attached to the Appendix of priority patent Application No. 63/387,130. A sensor for bioelectric information, e.g., a temperature sensor (not shown) typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference, and attached to the Appendix of priority patent Application No. 63/387,130.

In one embodiment, the positioning subsystem may include magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218, and attached to the Appendix of priority patent Application No. 63/387,130.

As noted above, the catheter 14 is coupled to the console, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter, and digitize signals from the catheter 14, including signals generated by sensors such as electrical, temperature, and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically includes an electroanatomic map generator, an image registration program, an image or data analysis program, and a graphical user interface configured to present graphical information on the monitor 29.

Typically, the system 10 includes other elements, which are not shown in the figures for sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 and maintained in a fixed position relative to the heart 12. Conventional pumps and lines for circulating liquids through the catheter 14 for cooling the ablation site are provided. The system 10 may receive image data form an external imaging modality, such as an MRI unit or the like and includes image processors that can be incorporated in or invoked by the processor 22 for generating and displaying images.

Figure 2A:
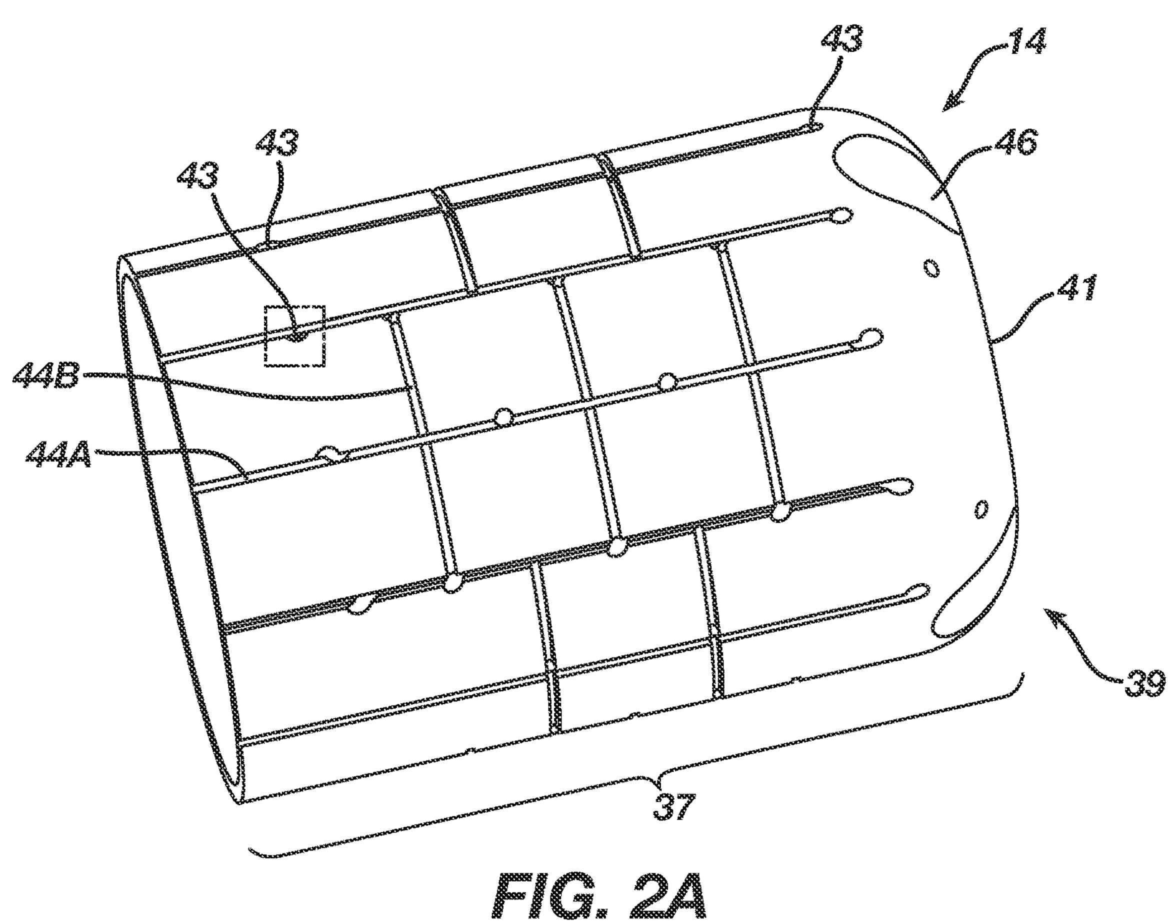
FIG. 2A is an illustration of the distal end portion of a catheter, according to aspects of the present invention.

Reference is now made to FIG. 2A, which is a view of distal end portion 37 of a catheter 39 adapted for cardiac ablation according to aspects of the present invention. The distal end portion 37 is a generally hollow cylinder, having a typical diameter of 2.5 mm. Tip 41 may be electrically conductive and function as an ablation electrode that is linked to an RF current generator. Typically, during ablation, heat is generated through resistive heating of the tissue. The heat conducts to surrounding regions including the ablation electrode. In order to dissipate the heart and dilute the surrounding blood, irrigation apertures 43 or pores are formed in the distal end portion 37. The apertures 43 typically have diameters that range from approximately 0.05 mm to 0.2 mm. irrigation fluid can be supplied through an internal conduit (not shown) that extends through the lumen of the catheter 39. The rate of flow the irrigation fluid is controlled by an irrigation module, and can vary from approximately 2 cc to approximately 30 cc per minute, but may be higher or lower than this range. A flow rate of 15 cc per minute is suitable for high flow requirements. By varying either or both of the rate of flow and the temperature of the irrigation fluid, the temperature about the distal end portion 37 can be controlled in accordance with the teachings of commonly assigned U.S. Pat. Nos. 10,327,859, 9,956,035, and 9,737,353, which are all herein incorporated by reference, and attached to the Appendix of priority patent Application No. 63/387,130.

As can be seen in FIG. 2A, the distal end portion 37 of catheter 39 may include one or more thermocouples 46 located at the tip 41 of the distal end portion 37. Thermocouples 46 can be any sensor suitable for obtaining electrophysiologic data from the body, e.g., temperature sensors for monitoring tissue ablation. Additionally, distal end portion 37 can include a plurality of grooves 44A oriented in a first direction (e.g., in a longitudinal direction) and a plurality of grooves 44B oriented in a second direction (e.g., in a circumferential direction). The plurality of grooves can serve the purpose of improving the distribution of irrigation fluid to a tissue site during an ablation procedure, thus avoiding the formation of hot spots that allow for "steam pops" that can damage tissue surrounding the ablation site. According to some embodiments, the first plurality of grooves (e.g., longitudinal grooves 44A) extend generally parallel to a longitudinal axis defined by catheter 39, and each longitudinal groove 44A may have at least two apertures 43 positioned within a respective longitudinal groove 44A, thereby facilitating redistribution of irrigation fluid along an outer surface of distal end portion 37 and the tissue ablation site. According to some embodiments, each of the second plurality of grooves (e.g., circumferential grooves 44B) may intersect with at least one of the longitudinal grooves 44A to define an aperture 43 at such intersection. According to some embodiments, the plurality of grooves 44 can be implemented in any geometric configuration. For example, the plurality of grooves 44A, 44B can form a mesh pattern, a diagonal pattern, and/or a random pattern. FIG. 2A shows an embodiment in which the first plurality of grooves 44A run in a longitudinal direction and the second plurality of grooves 44B run in a circumferential direction.

Figure 2B:
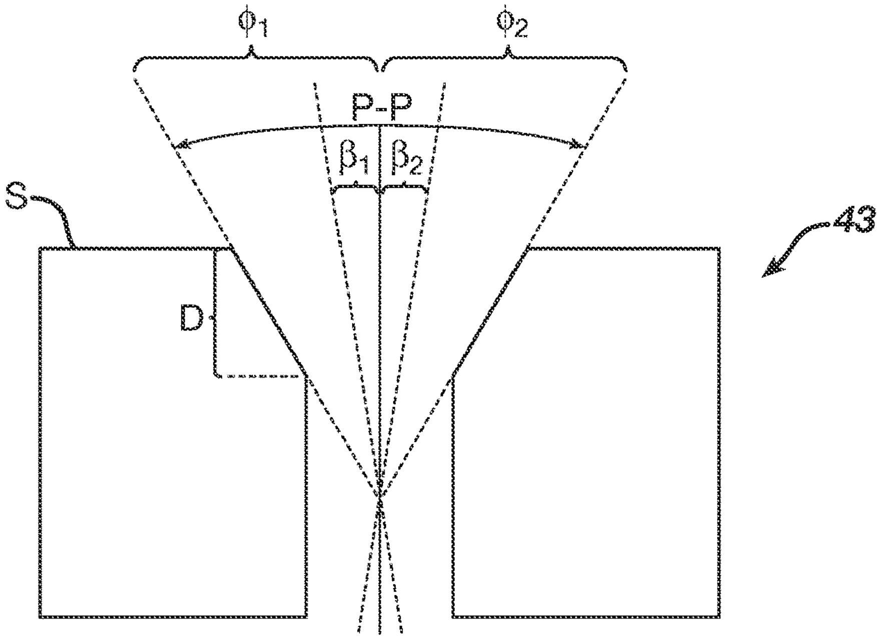
FIG. 2B is an illustration of angle offset and countersink depth for an aperture formed within a wall of the distal end portion of a catheter, according to aspects of the present invention.

An exemplary aperture 43 can be seen in more detail with respect to FIG. 2B. As shown in FIG. 2B, aperture 43 may be offset from a normal line P-P extending out of the surface of distal end portion 37 of catheter 39. The angle of offset of aperture 43 can be between $\beta_1$ in a first direction (e.g., a proximal direction) with respect to catheter 39 and $\beta_2$ in a second direction (e.g., a distal direction) with respect to catheter 39. According to some embodiments, the angle of $\beta_1$ can be between approximately 5 degrees and approximately 15 degrees. According to some embodiments, the angle of $\beta_2$ can be between approximately 5 degrees and approximately 15 degrees. Additionally, aperture 43 can be offset from a surface S of catheter distal end portion 37 by a distance D. According to some embodiments, aperture 43 can be countersunk into surface S of catheter distal end portion 37 in order to space aperture 43 from the surface of a tissue, thereby increasing irrigation efficiency and reducing hot spots during an ablation procedure. A first (e.g., left) countersink angle $\phi_1$ and a second (e.g., right) countersink angle $\phi_2$ are provided. According to some embodiments, the countersink angles $\phi_1$, $\phi_2$ can be between approximately 15 degrees and approximately 45 degrees, while in other embodiments, apertures 43 lack a countersink angle $\phi_1$, $\phi_2$. According to some embodiments, distance D can be any convenient distance to space aperture 43 from a tissue surface of a patient undergoing an ablative medical procedure. However, in a preferred embodiment, the distance D may measure between approximately 0.05 mm and 0.5 mm. The countersink defined by angles $\phi_1$, $\phi_2$ can serve to increase the surface diameter of aperture 43, which increases the force which needs to be applied to distal catheter end portion 37 against a tissue before apertures are blocked by the tissue surface. Therefore, countersinking improves the efficiency of irrigation through apertures 43 during an ablative procedure.

Figure 3:
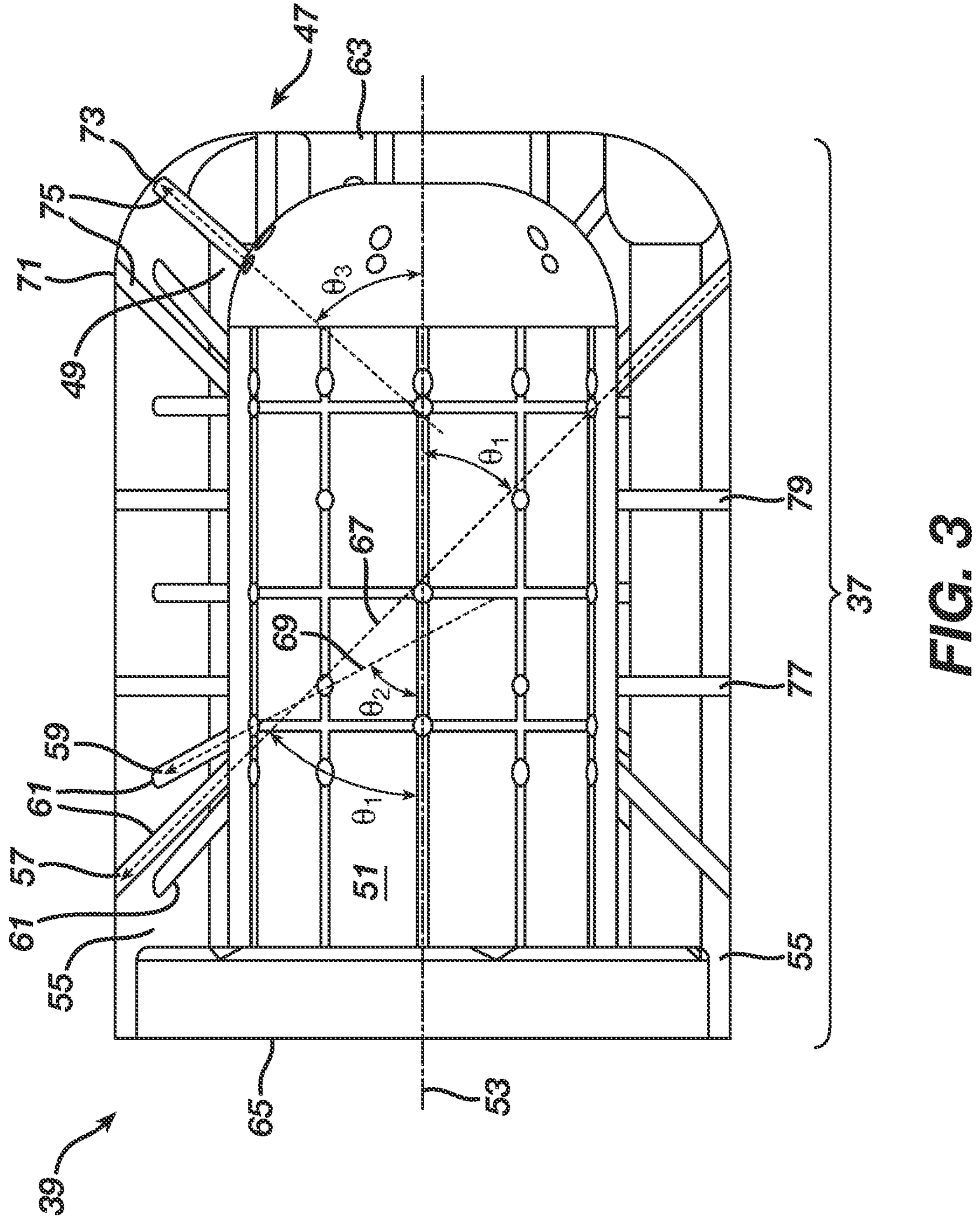
FIG. 3 is a longitudinal sectional view of the distal end portion shown in FIG. 2A, according to aspects of the present invention.

FIG. 3 illustrates a longitudinal partially cutaway view of the distal end portion 37 of a catheter 39, in accordance with an embodiment of the invention. The distal end portion 37 includes a hollow electrode 47 having a lumen 49 (as can be better seen in FIG. 4). The lumen 49 is partially occupied by a fluid delivery assembly 51. The distal end portion 37 has a longitudinal axis of symmetry 53. Apertures 57, 59 and other apertures 43 (FIG. 2A) are formed inside wall 55 of the electrode 47. The apertures place the exterior of the electrode 47 in fluid communication with the lumen 49 with channels, e.g., channels 61. Channels 61 are directed outward and backward. For purposes of this disclosure, the term "backward" refers to a direction from distal tip 63 generally toward to a proximal end 65 of the distal end portion 37. The term "outward" refers to a direction generally away from the axis of symmetry 53. Longitudinal axes 67, 69 of the apertures 57, 59 intersect the axis of symmetry 53 at angles of incidence $\theta_1$ and $\theta_2$, respectively. The angles of incidence of the outward, backward-directed apertures with the axis of symmetry 53 may vary from approximately 5 degrees to approximately 75 degrees, and are optimally around 45 degrees.

Irrigation fluid is delivered under pressure from an external source through the catheter into assembly 51. The irrigation fluid can exit the assembly 51 into the lumen 49 of the electrode 47. The irrigation fluid then exits the lumen 49 via the aperture 57, 59 in direction indicated by arrows in the axes 67, 69. Irrigation fluid so directed cools an area diagonally behind and outward of the distal end portion 37. Similarly, outward, forward-directed apertures 71, 73 direct the irrigation fluid in directions specified by the angulations of their respective channels 75 with respect to the axis of symmetry 53, e.g., angle of incidence $\theta_3$ in the case of aperture 73 to deliver fluid diagonally forward and outward of the distal end portion 37. Additionally, the distal end portion 37 can include conventional sideward directed apertures, e.g., apertures 77, 79, which direct the irrigation fluid outward and sideward from the distal end portion 37. The inclusion of grooves 44A, 44B in the surface of distal end portion 37 facilitate the optimal distribution of irrigation fluid throughout the ablation site and areas proximal to the ablation site during a medical procedure. The grooves prevent the formation of hot spots surrounding the treatment site, and reduce the incidence of "steam pops" that can damage surrounding tissue.

Figure 4:
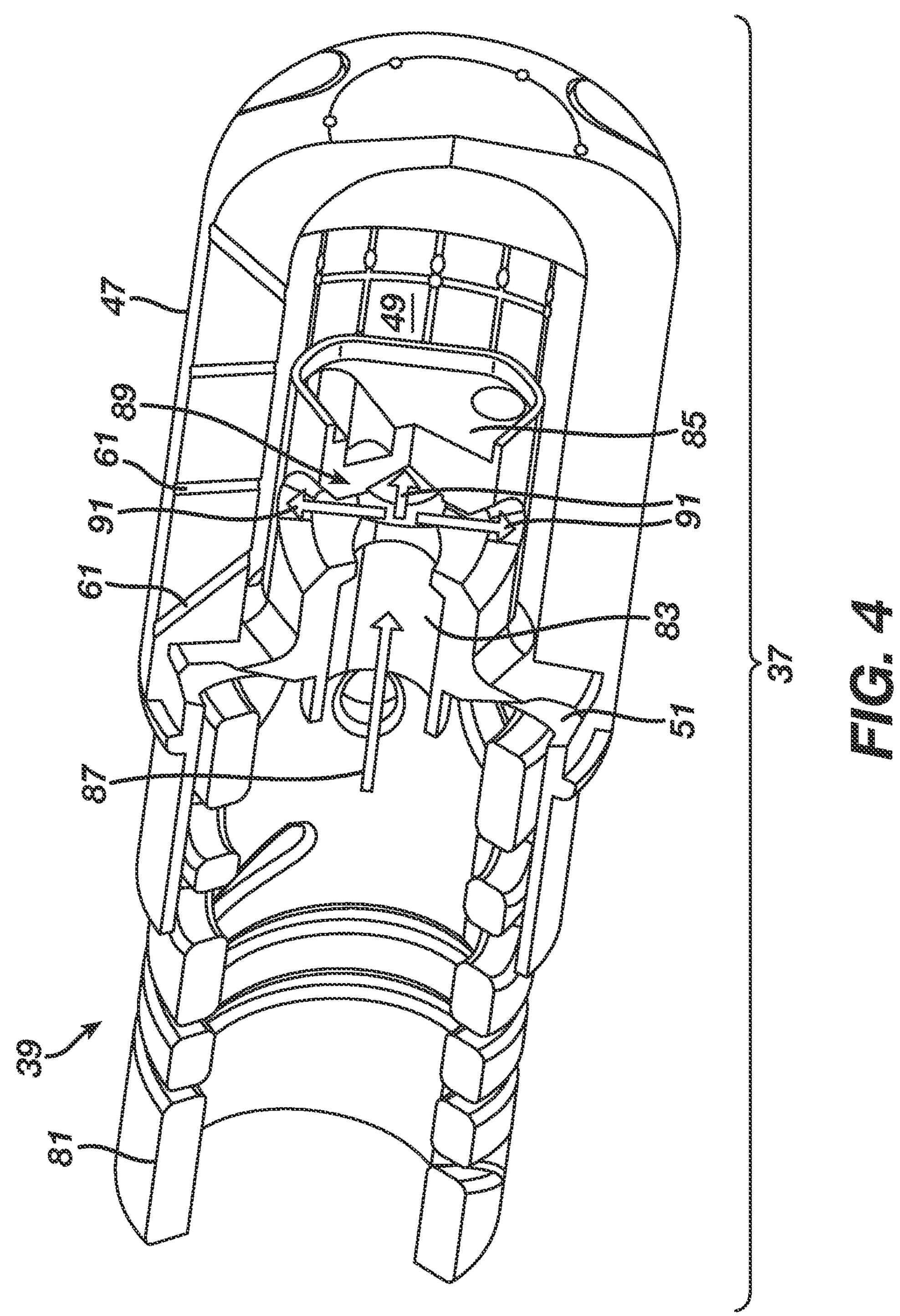
FIG. 4 is a cut-away sectional view of a distal segment of a catheter showing a fluid-directing assembly, according to aspects of the present invention.

Shown in FIG. 4 is a cut-away sectional view of distal end portion 37 of catheter 39, in accordance with an embodiment of the invention. Assembly 51 mates with segment 81 of catheter 39 and with the electrode 47. The assembly 51 includes an axial lumen 83 that conducts irrigation fluid distally towards a blocking terminus 85 that prevents the irrigation fluid from continuing in a forward direction. The irrigation fluid flow is indicated by an arrow 87. At the terminus 85 a plurality of channels 89 branch trans-axially outward at 90° angles to the axial lumen 83, diverting the flow outward as indicated by arrows 91. The irrigation fluid enters the lumen 49 transverse to the axis of the catheter 39, generally toward the lateral channels in the electrode 47, such as the channels 61.

If the irrigation path exited the lumen 83 in alignment with the axis of symmetry 53 (as shown in FIG. 3), irrigation flow through the channels 61 would be disfavored, because the flow would be required to reverse course, and to turn more than 90 degrees to enter the proximally angled channels, such as the channels 61. It is an advantage of the arrangement of FIG. 4 that the irrigation flow is relatively more evenly distributed to all the holes in electrode 47 than if the flow exited the assembly 51 in a forward direction.

Figure 5:
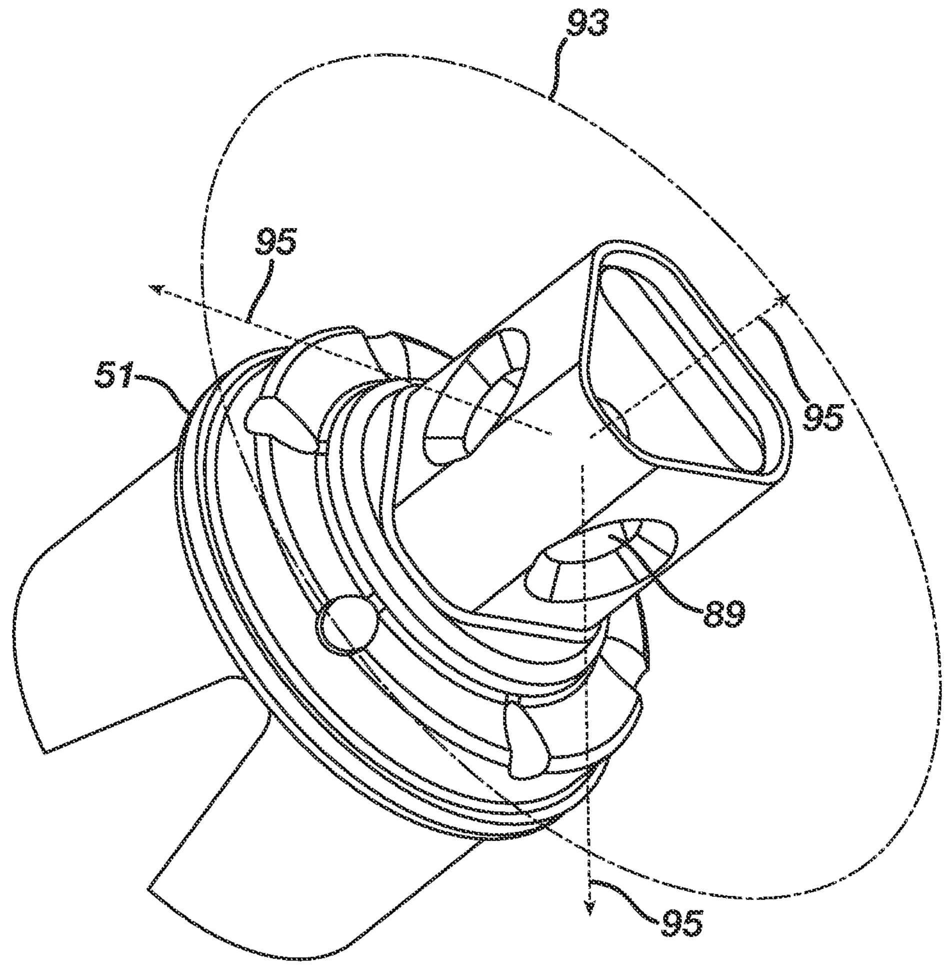
FIG. 5 is an oblique elevation of the fluid-directing assembly shown in FIG. 4, according to aspects of the present invention.

FIG. 5 shows an oblique elevation view of the assembly 51, showing the channels 89 in accordance with an embodiment of the invention. In this embodiment, there are three channels 89, which lie in a plane 93, and are distributed about the axis of the catheter at 1200 angles. Direction of flow from the lumen 83 to exits the assembly 51 is indicated by broken lines 95. Other embodiments may have a different number of channels 89, typically varying from two to twelve channels.

Figure 6:
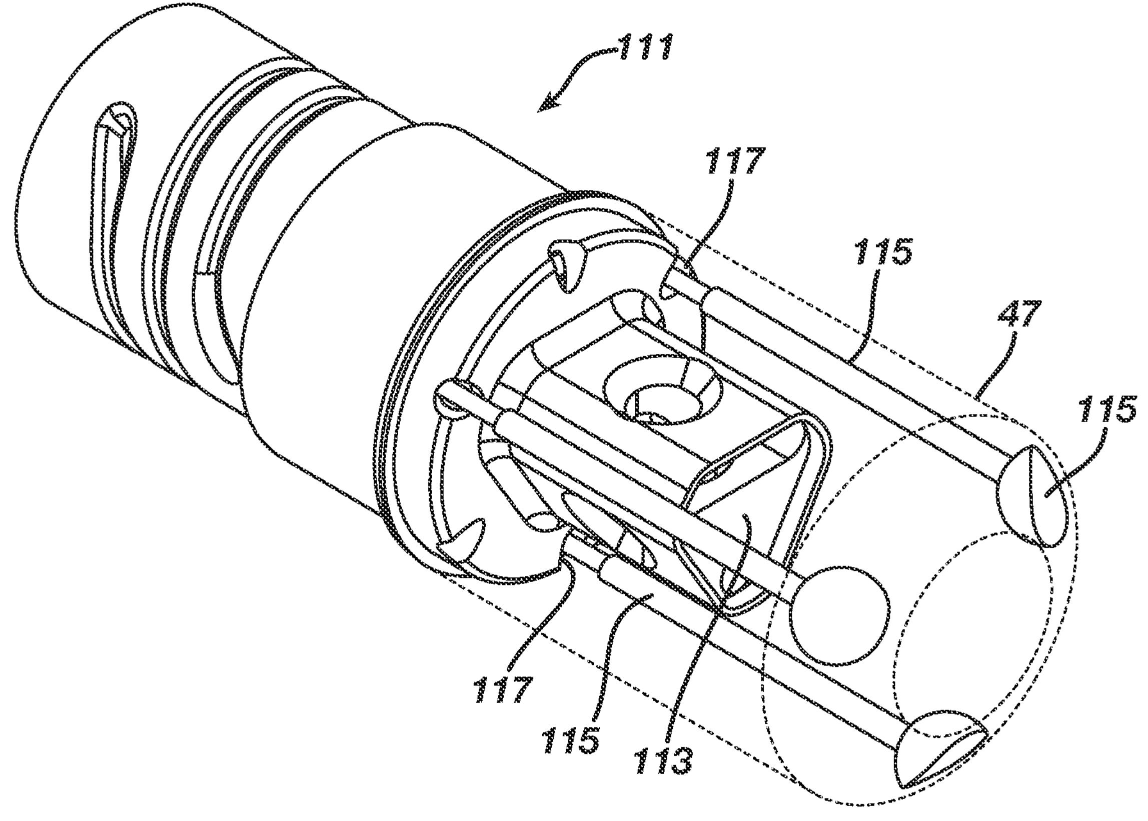
FIG. 6 is an oblique elevation of the distal end of a catheter, according to aspects of the present invention.

With respect to FIG. 6, an oblique elevation of the distal end of catheter 111, in accordance with an alternate embodiment of the invention. Assembly 113 is disposed within electrode 47. In addition to the fluid diversion function described above, the assembly 113 has a second function of supporting sensors 115 through slots 117. The sensors can be any sensor suitable for obtaining electrophysiologic data from the body, e.g., temperature sensors for monitoring tissue ablation. The slots 117 allow passage of the sensors through assembly 113 into the wall cavity of electrode 47. In operation, while the catheter is in the heart, different sensors may be inserted through the catheter through the slots 117 and retracted as dictated by the needs of the medical procedure.

Figure 7:
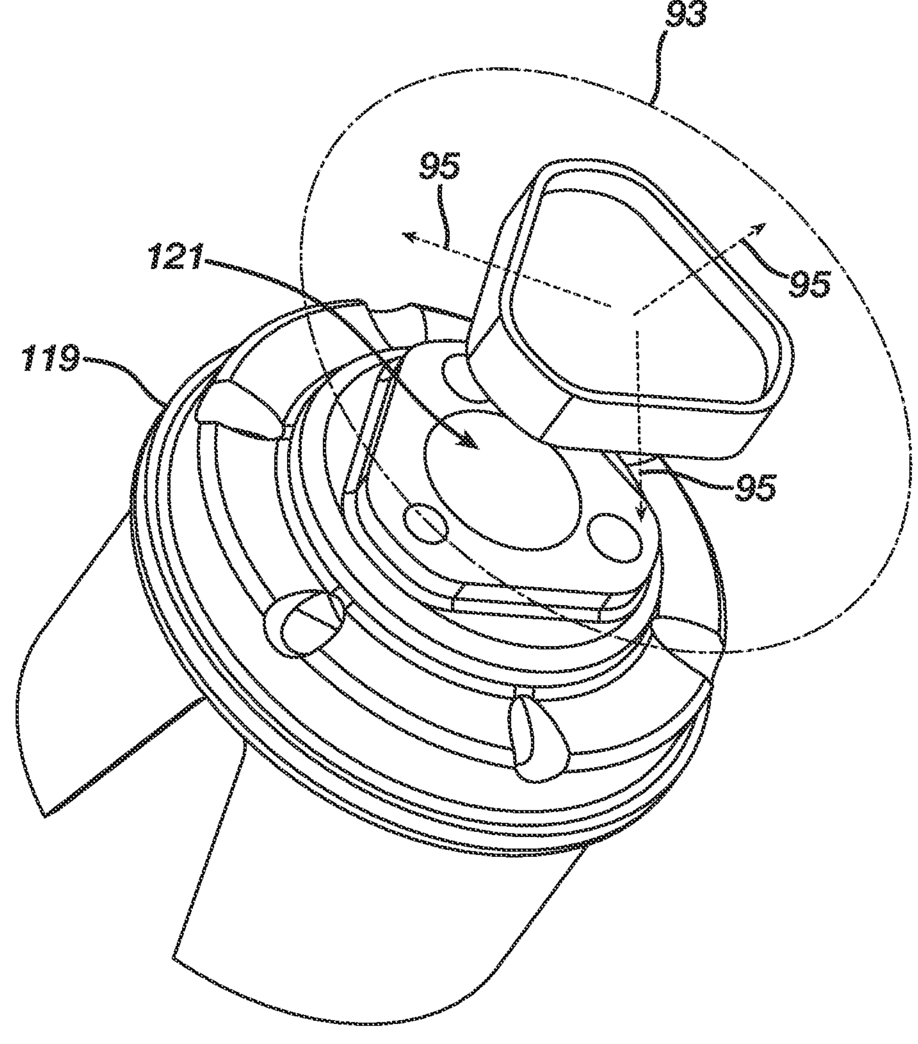
FIG. 7 is an oblique elevation of the fluid-directing assembly shown in FIG. 4, according to aspects of the present invention.

FIG. 7 shows an oblique view of an assembly 119, in accordance with an alternate embodiment of the invention. FIG. 7 is similar to FIG. 5, except FIG. 7 shows a single trans-axial channel 121 that forms a slot, extending about a sector of the circumference of lumen 83 that can be 360 degrees as shown in FIG. 7. There may be one slot as shown in FIG. 7. Alternatively, more than one slot may be distributed about the circumference of the assembly.

Figure 8:
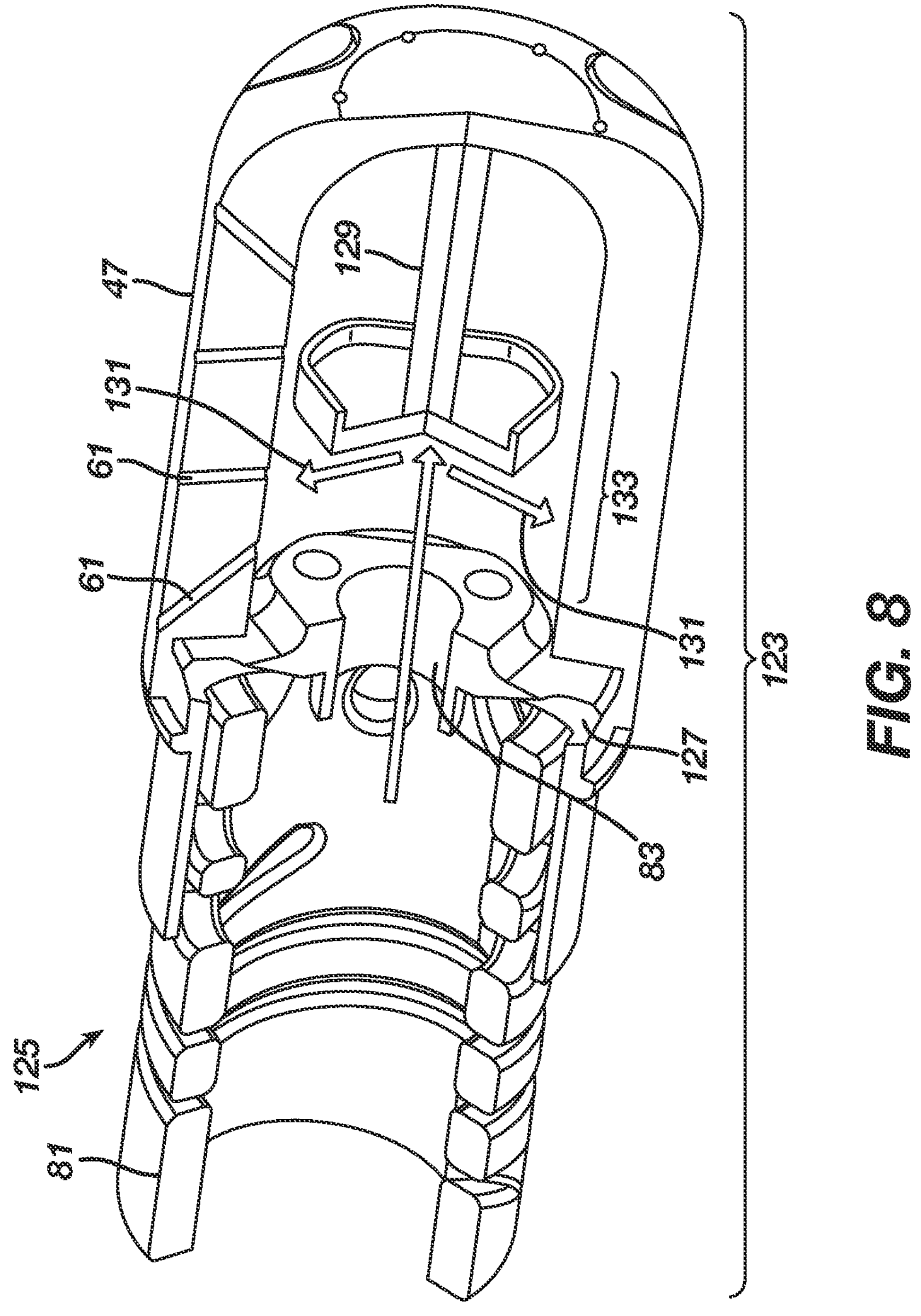
FIG. 8 is a cut-away sectional view of a distal segment of a catheter showing a fluid-direction assembly, according to aspects of the present invention.

FIG. 8 shows yet another alternative embodiment of the invention. In FIG. 8, a single gap provides flow transverse to the axis of symmetry in a full 360 degree spread. FIG. 8 shows a cut-away sectional view of distal end portion 124 of catheter 125 in accordance with an alternative embodiment of the invention. Assembly 127 mates with segment 81 of the catheter 125 and with the electrode 47. Unlike the embodiment shown in FIG. 4, the assembly 127 lacks channels 89 and the blocking terminus 85. Instead the flow exits the distal end of the assembly 127 and continues distally within the lumen 49, striking a baffle 129, which is spaced apart from the assembly 127 by a gap 133. The baffle 129 deflects the flow of irrigation fluid transverse to the axis of symmetry toward the wall of the electrode 47 in a 360 degree radial spread, as indicated by arrows 131. Thereafter, the irrigation fluid enters the channels 61 and the other channels that penetrate the wall of electrode 47 as described in more detail with respect to FIG. 4.

FIG. 9 is a flowchart of an exemplary method 900 of treating a patient using a catheter according to aspects of the present invention. In block 902, the method includes providing a probe. The probe may have an elongated catheter body that defines a longitudinal axis and a distal tip that is coupled to the distal end of the elongated catheter body. The distal tip can have an outer surface, a cavity, a proximal end, a distal end, and a wall having a plurality of apertures 43 connecting the outer surface and the cavity. The apertures can be arranged in a grid that has columns that are generally parallel to the longitudinal axis and rows that are generally perpendicular to the longitudinal axis. The wall of the distal tip can have a plurality of longitudinal grooves 44A and a plurality of circumferential grooves 44B. The distal tip can include at least one electrode that is coupled to an energy source to apply ablative current to a tissue. The probe also can include a fluid-directing assembly that has an axial channel that is in fluid communication with the cavity of distal tip, and thereby the plurality of apertures.

In block 904, the method may include providing irrigation fluid into the axial channel of the fluid-directing assembly. In block 906, the method may include directing the irrigation fluid from the axial channel through one or more trans-axial channels that are perpendicular to the axial channel, through the cavity of the electrode 47 and into the tissue through the plurality of apertures 43. In block 908, the method can include directing the irrigation fluid from the plurality of apertures 43 and through the plurality of longitudinal grooves 44A and the plurality of circumferential grooves 44B. In block 910, the method can include pressing the distal tip 41 against the tissue until the wall 55 of the distal tip is compressed against the tissue. In block 912, the method can include causing the irrigation fluid to flow through the plurality of apertures 43 without becoming blocked due to each of the plurality of apertures 43 being recessed from the outer surface of the distal tip 41.

In some embodiments, a first portion of the plurality of apertures are oriented at a proximal angle with respect to the longitudinal axis and the first portion may be positioned on a row of apertures that is proximal the proximal end of distal tip 41. For example, the angled apertures may provide improved irrigation fluid flow to an area proximate the proximal end of distal tip 41. In some embodiments, the proximal angle can be between approximately 5 degrees and approximately 15 degrees.

In some embodiments, a second portion of the plurality of apertures can be oriented at a distal angle with respect to the longitudinal axis. The second portion of apertures can be positioned on a row that is proximate the distal end of distal tip 41. For example, the angled apertures may provide improved irrigation fluid flow to an area proximate the distal end of distal tip 41. In some embodiments, the distal angle can be between approximately 5 degrees and approximately 15 degrees.

In some embodiments, each of the plurality of apertures can be recessed from the outer surface of distal tip 41 by a distance D. The distance D can be between approximately 0.05 mm and 0.2 mm.

It will be appreciated by persons skilled in the pertinent art that the present invention is not limited to what has been particularly shown and described herein. Rather, the scope of the present invention includes both combinations and sub-combinations of the various features described herein, as well as variations and modifications thereof that are not in the prior art, which would occur to persons skilled in the pertinent art upon reading the foregoing description.

The following clauses list non-limiting embodiments of the disclosure:

Clause 1: A medical device, comprising: an elongated catheter body defining a longitudinal axis; a distal tip electrode coupled to a distal end of the elongated catheter body, the distal tip electrode having an outer surface, a cavity, a proximal end, a distal end, and a wall having a plurality of apertures connecting the outer surface and the cavity, the apertures arranged in a grid having columns generally parallel to the longitudinal axis and rows generally perpendicular to the longitudinal axis; a plurality of longitudinal grooves formed in the wall of the distal tip electrode so that each longitudinal groove extends generally parallel to the longitudinal axis, each of the plurality of longitudinal grooves having at least two apertures of the plurality of apertures positioned within a respective longitudinal groove; and a first plurality of circumferential grooves formed in the wall of the distal tip electrode so that each circumferential groove intersect with at least one of the longitudinal grooves to define an aperture at such intersection.

Clause 2: The medical device of clause 1, further comprising one or more sensing elements disposed on the distal end of the distal tip electrode, each of the one or more sensing elements positioned in between two adjacent longitudinal grooves.

Clause 3: The medical device of clauses 1 or 2, each of the plurality of apertures recessed from the outer surface of the distal tip electrode by a distance D.

Clause 4: The medical device of clause 3, wherein the distance D is between approximately 0.05 mm and approximately 0.2 mm.

Clause 5: The medical device of any of clauses 1 to 4, wherein a first portion of the plurality of apertures are oriented at a proximal angle with respect to the longitudinal axis, the first portion positioned on a row proximate the proximal end of the distal tip electrode.

Clause 6: The medical device of any of clauses 1 to 5, wherein a second portion of the plurality of apertures are oriented at a distal angle with respect to the longitudinal axis, the second portion positioned on a row proximate the distal end of the distal tip electrode.

Clause 7: The medical device of any of clauses 1 to 6, the apertures configured to direct an irrigation fluid.

Clause 8: The medical device of any of clauses 1 to 7, at least one of the first plurality of circumferential grooves having at least two apertures of respective non-adjacent columns positioned within a respective circumferential groove of the first plurality of circumferential grooves.

Clause 9: The medical device of any of clauses 1 to 8, the plurality of longitudinal grooves having four apertures of the plurality of apertures positioned within the respective longitudinal groove.

Clause 10: The medical device of any of clauses 1 to 9, the plurality of longitudinal grooves and the first plurality of circumferential grooves forming a grid-pattern on the wall of the distal tip electrode.

Clause 11: The medical device of any of clauses 1 to 10, further comprising:

a fluid-directing assembly having an axial channel that is in fluid communication with the cavity of the distal tip electrode and thereby the plurality of apertures; and a blocking terminus fixed within the cavity of the distal tip electrode that is configured to block a flow of fluid along a longitudinal axis, direct the flow of fluid through at least one trans-axial channel that is transverse to the axial channel, and direct the flow of fluid through the plurality of apertures.

Clause 12: The medical device of clause 11, the fluid-directing assembly having between two and twelve trans-axial channels.

Clause 13: The medical device of clause 11, the fluid-directing assembly having exactly one trans-axial channel.

Clause 14: The medical device of clause 11, the distal tip electrode comprises at least one electrode coupled to an energy source to apply an ablative current to a tissue; the fluid-directing assembly is in fluid communication with an irrigation pump that delivers irrigation fluid to the fluid-directing assembly; and in response to increasing power to the at least one electrode to approximately 90 W, increasing an irrigation flow rate of the irrigation pump.

Clause 15: The medical device of clause 14, the irrigation flow rate increased by closing a loop with the irrigation pump.

Clause 16: A medical device, comprising: an elongated catheter body defining a longitudinal axis; a distal tip coupled to a distal end of the elongated catheter body, the distal tip having an outer surface, a cavity, a proximal end, a distal end, and a wall comprising an end portion and a sidewall portion, the sidewall portion of the wall having a plurality of apertures connected the outer surface and the cavity; the distal tip comprises at least one electrode coupled to an energy source to apply an ablative current to a tissue inside a body of a patient; a first plurality of grooves formed in the wall of the distal tip, each of the first plurality of grooves formed in a first orientation with respect to the longitudinal axis; a second plurality of grooves formed in the wall of the distal tip, the second plurality of grooves formed in a second orientation with respect to the longitudinal axis; each of the first plurality of grooves and the second plurality of grooves having at least two respective apertures of the plurality of apertures positioned within a respective groove; a fluid-directing assembly having an axial channel that is in fluid communication with the cavity of the distal tip and thereby the plurality of apertures; and a blocking terminus fixed within the cavity of the distal tip that is configured to block a flow of fluid along the longitudinal axis, direct the flow of fluid through at least one trans-axial channel that is transverse to the axial channel, and direct the flow of fluid through the plurality of apertures.

Clause 17: The medical device of clause 16, the first plurality of grooves and the second plurality of grooves each forming diagonal grooves with respect to the longitudinal axis in the wall of the distal tip.

Clause 18: The medical device of clause 16, the first plurality of grooves and the second plurality of grooves arranged in a mesh pattern of grooves in the wall of the distal tip.

Clause 19: The medical device of clause 16, the first plurality of grooves and the second plurality of grooves arranged in a randomized pattern in the wall of the distal tip.

Clause 20: The medical device of any of clauses 16 to 19, further comprising one or more sensing elements disposed on the distal tip.

Clause 21: The medical device of any of clauses 16 to 20. the fluid-directing assembly is in fluid communication with an irrigation pump that delivers irrigation fluid to the fluid-directing assembly; and in response to increasing power to the at least one electrode to approximately 90 W, increasing an irrigation flow rate of the irrigation pump.

Clause 22: The medical device of any of clauses 16 to 21, each of the plurality of apertures recessed from the outer surface of the distal tip by a distance D.

Clause 23: The medical device of clause 22, wherein the distance D is between approximately 0.05 mm and approximately 0.2 mm.

Clause 24: The medical device of any of clauses 16 to 23, wherein a first portion of the plurality of apertures are oriented at a proximal angle with respect to the longitudinal axis, the first portion positioned on a row proximate the proximal end of the distal tip.

Clause 25: The medical device of any of clauses 16 to 24, wherein a second portion of the plurality of apertures are oriented at a distal angle with respect to the longitudinal axis, the second portion positioned on a row proximate the distal end of the distal tip.

Clause 26: The medical device of any of clauses 16 to 25, the apertures configured to direct an irrigation fluid to a tissue inside the body.

Clause 27. A method of directing irrigation fluid from a medical probe, comprising: providing a probe having an elongated catheter body defining a longitudinal axis, a distal tip coupled to a distal end of the elongated catheter body, the distal tip having an outer surface, a cavity, a proximal end, a distal end, a wall having a plurality of apertures connecting the outer surface and the cavity, the apertures arranged in a grid having columns generally parallel to the longitudinal axis and rows generally perpendicular to the longitudinal axis, the wall having a plurality of longitudinal grooves and a plurality of circumferential grooves, the distal tip comprising at least one electrode that is coupled to an energy source to apply an ablative current to a tissue, and a fluid-directing assembly having an axial channel that is in fluid communication with the cavity of the distal tip and thereby the plurality of apertures; providing irrigation fluid into an axial channel of the fluid-directing assembly directing the irrigation fluid from the axial channel through one or more trans-axial channels perpendicular to the axial channel through the cavity of the electrode and into the tissue through the plurality of apertures; and directing the irrigation fluid from the plurality of apertures and through the plurality of longitudinal grooves and the plurality of circumferential grooves.

Clause 28: The method of clause 27, wherein a first portion of the plurality of apertures are oriented at a proximal angle with respect to the longitudinal axis, the first portion positioned on a row proximate the proximal end of the distal tip.

Clause 29: The method of clause 27 or 28, wherein a second portion of the plurality of apertures are oriented at a distal angle with respect to the longitudinal axis, the second portion positioned on a row proximate the distal end of the distal tip.

Clause 30: The method of any of clauses 27 to 29, each of the plurality of apertures recessed from the outer surface of the distal tip by a distance D.

Clause 31: The method of clause 30, wherein the distance D between approximately 0.05 mm and approximately 0.2 mm.

Clause 32: The method of clauses 30 or 31, further comprising: pressing the distal tip against the tissue until the wall of the distal tip is compressed against the tissue; and causing the irrigation fluid to flow through the plurality of apertures without becoming blocked due to each of the plurality of apertures being recessed from the outer surface of the distal tip.

What is claimed is:

1. A medical device, comprising:

an elongated catheter body defining a longitudinal axis;

a distal tip electrode coupled to a distal end of the elongated catheter body, the distal tip electrode having an outer surface, a cavity, a proximal end, a distal end, and a wall having a plurality of holes connecting the outer surface and the cavity, the holes arranged in a grid having columns generally parallel to the longitudinal axis and rows generally perpendicular to the longitudinal axis;

a plurality of longitudinal grooves formed in the outer surface of the distal tip electrode so that each longitudinal groove extends generally parallel to the longitudinal axis, each of the plurality of longitudinal grooves having at least two holes of the plurality of holes positioned within a respective longitudinal groove; and a first plurality of circumferential grooves formed in the outer surface of the distal tip electrode so that each circumferential groove intersects with at least one of the longitudinal grooves to define a hole at such intersection.

2. The medical device of claim 1, further comprising one or more sensing elements disposed on the distal end of the distal tip electrode, each of the one or more sensing elements positioned in between two adjacent longitudinal grooves.

3. The medical device of claim 1, each of the plurality of holes recessed from the outer surface of the distal tip electrode by a distance D.

4. The medical device of claim 3, wherein the distance D is between approximately 0.05 mm and approximately 0.2 mm.

5. The medical device of claim 1, wherein a first portion of the plurality of holes are oriented at a proximal angle with respect to the longitudinal axis, the first portion positioned on a row proximate the proximal end of the distal tip electrode.

6. The medical device of claim 1, wherein a second portion of the plurality of holes are oriented at a distal angle with respect to the longitudinal axis, the second portion positioned on a row proximate the distal end of the distal tip electrode.

7. The medical device of claim 1, the holes configured to direct an irrigation fluid.

8. The medical device of claim 1, at least one of the first plurality of circumferential grooves having at least two holes of respective non-adjacent columns positioned within a respective circumferential groove of the first plurality of circumferential grooves.

9. The medical device of claim 1, the plurality of longitudinal grooves having four holes of the plurality of holes positioned within the respective longitudinal groove.

10. The medical device of claim 1, the plurality of longitudinal grooves and the first plurality of circumferential grooves forming a grid-pattern on the wall of the distal tip electrode.

11. The medical device of claim 1, further comprising:

a fluid-directing assembly having an axial channel that is in fluid communication with the cavity of the distal tip electrode and thereby the plurality of holes; and a blocking terminus fixed within the cavity of the distal tip electrode that is configured to block a flow of fluid along the longitudinal axis, direct the flow of fluid through at least one trans-axial channel that is transverse to the axial channel, and direct the flow of fluid through the plurality of holes.

12. The medical device of claim 11, the distal tip electrode comprises at least one electrode coupled to an energy source to apply an ablative current to a tissue;

the fluid-directing assembly is in fluid communication with an irrigation pump that delivers irrigation fluid to the fluid-directing assembly; and in response to increasing power to the at least one electrode to approximately 90 W, increasing an irrigation flow rate of the irrigation pump.

13. A medical device, comprising:

an elongated catheter body defining a longitudinal axis;

a distal tip coupled to a distal end of the elongated catheter body, the distal tip having an outer surface, a cavity, a proximal end, a distal end, and a wall comprising an end portion and a sidewall portion, the sidewall portion of the wall having a plurality of holes connected to the outer surface and the cavity;

the distal tip comprises at least one electrode coupled to an energy source to apply an ablative current to a tissue inside a body of a patient;

a first plurality of grooves formed in the outer surface of the distal tip, each of the first plurality of grooves formed in a first orientation with respect to the longitudinal axis;

a second plurality of grooves formed in the outer surface of the distal tip, the second plurality of grooves formed in a second orientation with respect to the longitudinal axis;

each of the first plurality of grooves and the second plurality of grooves having at least two respective holes of the plurality of holes positioned within a respective groove;

a fluid-directing assembly having an axial channel that is in fluid communication with the cavity of the distal tip and thereby the plurality of holes; and a blocking terminus fixed within the cavity of the distal tip that is configured to block a flow of fluid along the longitudinal axis, direct the flow of fluid through at least one trans-axial channel that is transverse to the axial channel, and direct the flow of fluid through the plurality of holes.

14. The medical device of claim 13, the first plurality of grooves and the second plurality of grooves each forming diagonal grooves with respect to the longitudinal axis in the wall of the distal tip.

15. The medical device of claim 13, the first plurality of grooves and the second plurality of grooves arranged in a mesh pattern of grooves in the wall of the distal tip.

16. The medical device of claim 13, the first plurality of grooves and the second plurality of grooves arranged in a randomized pattern in the wall of the distal tip.

17. The medical device of claim 13, the fluid-directing assembly is in fluid communication with an irrigation pump that delivers irrigation fluid to the fluid-directing assembly; and in response to increasing power to the at least one electrode to approximately 90 W, increasing an irrigation flow rate of the irrigation pump.

18. The medical device of claim 13, wherein a first portion of the plurality of holes are oriented at a proximal angle with respect to the longitudinal axis, the first portion positioned on a row proximate the proximal end of the distal tip.

19. The medical device of claim 13, wherein a second portion of the plurality of holes are oriented at a distal angle with respect to the longitudinal axis, the second portion positioned on a row proximate the distal end of the distal tip.

20. A method of directing irrigation fluid from a medical probe, comprising:

providing a probe having an elongated catheter body defining a longitudinal axis, a distal tip coupled to a distal end of the elongated catheter body, the distal tip having an outer surface, a cavity, a proximal end, a distal end, a wall having a plurality of holes connecting the outer surface and the cavity, the holes arranged in a grid having columns generally parallel to the longitudinal axis and rows generally perpendicular to the longitudinal axis, a plurality of longitudinal grooves and a plurality of circumferential grooves formed in the outer surface, the distal tip comprising at least one electrode that is coupled to an energy source to apply an ablative current to a tissue, and a fluid-directing assembly having an axial channel that is in fluid communication with the cavity of the distal tip and thereby the plurality of holes;

providing irrigation fluid into an axial channel of the fluid-directing assembly;

directing the irrigation fluid from the axial channel through one or more trans-axial channels perpendicular to the axial channel through the cavity of the electrode and into the tissue through the plurality of holes; and directing the irrigation fluid from the plurality of holes and through the plurality of longitudinal grooves and the plurality of circumferential grooves.

* * * * *